United States Patent [19]  [11]  4,269,516
Lübbers et al.  [45] * May 26, 1981

[54] OPTODE

[75] Inventors: Dietrich W. Lübbers, Dortmund; Norbert Optiz, Bochum, both of Fed. Rep. of Germany

[73] Assignee: Max-Planck-Gesellschaft zur Förderung der Wissenschaften E.V., Göttingen, Fed. Rep. of Germany

[*] Notice: The portion of the term of this patent subsequent to Jan. 18, 1994, has been disclaimed.

[21] Appl. No.: 817,108

[22] Filed: Jul. 19, 1977

[30] Foreign Application Priority Data

Jul. 21, 1976 [DE] Fed. Rep. of Germany ....... 2632710

[51] Int. Cl.³ ............................................ G01N 21/84
[52] U.S. Cl. ...................................... 356/427; 356/39
[58] Field of Search .................... 356/196, 39, 41, 85, 356/427; 128/2 G, 2 L, 214 B, DIG. 23; 23/230 B, 232 R, 254 R

[56] References Cited

U.S. PATENT DOCUMENTS

| 3,825,342 | 7/1974 | Lubbers et al. | 356/41 |
| 3,997,272 | 12/1976 | George | 356/196 |
| 4,003,707 | 1/1977 | Lubbers et al. | 356/39 |
| 4,013,417 | 3/1977 | Raffaele | 23/230 B |

Primary Examiner—John K. Corbin
Assistant Examiner—B. Wm. de los Reyes
Attorney, Agent, or Firm—Michael J. Striker

[57] ABSTRACT

Monochromatic excitation light penetrates an indicator in an indicator space. The indicator space is closed off at the side to be brought into contact with the substance to be analyzed by means of a membrane permeable for the component of the substance whose concentration is to be ascertained. The side of the indicator space facing the light-measuring unit of the device is radiation-transmissive. The indicator is set into motion during the measurement operation. Alternatively, the substance to be analyzed, on the other side of the permeable membrane, is set into convective motion during the measurement operation. As a further alternative, both the indicator and the substance to be analyzed are set into motion in mutually perpendicular directions, which however are both parallel to the permeable membrane.

14 Claims, 4 Drawing Figures

OPTODE

BACKGROUND OF THE INVENTION

The invention relates to the optical measurement of the concentration of a component of interest in a substance to be analyzed, for example the concentration of oxygen in human blood. Typically, this type of optical measuring apparatus includes a housing provided with a monochromator which furnishes monochromatic excitation radiation, an indicator chamber containing an indicator through which the monochromatic excitation radiation passes in order to excite the indicator, and a light-measuring unit which receives the radiation emitted from the indicator in order to determine its spectral (color or fluorescent) response to the concentration of the component of interest. The indicator space is closed off at the side facing the substance to be analyzed by means of a membrane which is permeable for the component whose concentration is to be ascertained; the indicator space is closed off at the side facing the monochromator by means of a wall which is transmissive for the measuring radiation.

With measuring apparatuses of this type, a difficulty results from the fact that the layer of indicator adjoining the permeable membrane in question comes relatively fast into combination with the component whose concentration is to be ascertained; in contrast, the layers of the indicator more remote from the permeable membrane are reached by the component of interest only as the component of interest diffuses, and relatively slowly, into these more remote layers. Accordingly, the equilibrium state which should be reached in order that the concentration read-out of the device be sufficiently accurate, requires a relatively long time to be established.

SUMMARY OF THE INVENTION

It is a general object of the invention to increase the speed at which the component whose concentration is to be ascertained becomes distributed in the optode.

According to one concept of the invention, this is accomplished by setting the indicator within the optode into motion. In this way, the slowly performed diffusive distribution of the component of interest within the indicator space is circumvented, and the speed at which a uniform or steady distribution of the component of interest within the indicator space becomes established is increased.

According to one concept of the invention, a mechanical oscillatory-motion generator is mechanically coupled to the optode and is used to set the indicator into oscillatory motion. Mechanically generated oscillatory motion of the indicator can be achieved even in very thin and flat optodes, particularly for example if the mechanical oscillatory-motion generator is a generator of ultrasonic sound.

According to another concept of the invention, the fluid indicator is provided with a material which can be set into motion by means of electrical or magnetic oscillatory fields, to set the indicator within the optode into oscillatory motion using such fields.

A further concept of the invention is to set the indicator within the optode into motion by deformation of the optode itself.

Another difficulty involved in the use of an optode resides in the fact that the layers of the substance to be analyzed (whether a gas or a liquid) which directly adjoin the membrane permeable for the component of interest, quickly become depleted of the component of interest, due to the passage of the component of interest through the permeable membrane into the indicator space. In this situation too, diffusion processes replenish the depleted zone. However, because the diffusion processes proceed very slowly and are proportional to the concentration gradient, it is a further object of the invention to increase the speed at which the steady or equilibrium value of the concentration gradient is established.

This additional object can be achieved, according to a further concept of the invention, by setting the substance to be analyzed containing the component of interest into convective motion. A particularly simple way of doing this is to provide, within the chamber accommodating the substance to be analyzed, an agitator which is magnetically driven, for example driven by an electric motor which could be located outside the chamber. Alternatively, the convective motion of the substance to be analyzed is established by continually recirculating the substance to be analyzed out of and then back into the chamber which adjoins the aforementioned permeable membrane.

As one contemplated possibility, the chamber containing the substance to be analyzed can be formed together with the optode into a single component, and the substance to be analyzed in such chamber can be agitated as described above. However, another very advantageous possibility is to use the optode as a separate component. In that case, the indicator could be contained between one membrane which is non-permeable for the component of interest and another membrane which is permeable for the component of interest; the permeable membrane would then be provided at its rim with an adhesive layer. In this way, the substance to be analyzed (for example, blood), can be passed through a conduit provided with an opening corresponding to the rim configuration of the permeable membrane; to measure the concentration of the component of interest, the permeable membrane would be pressed into place against the aforementioned opening in the conduit, with the adhesive layer at the rim of the permeable membrane firmly engaging the boundary of the conduit opening, both to hold the optode in place and to seal the connection between the optode and the conduit. Then, the substance to be analyzed transmitted through the conduit would flow along the permeable membrane, and the component of interest would penetrate through the permeable membrane into the indicator space within the optode. Using this technique, physical parameters besides concentration can be measured, e.g., pressure, temperature, and the like, it only being necessary to use for each such measurement an appropriate one of the conventional indicators known in the art.

With the expedient just mentioned, it would also be possible to press the permeable membrane directly against the skin or other tissue through which, for example, blood is being perfused, in which case the aforementioned adhesive at the rim of the permeable membrane serves both to firmly seure the optode to the tissue of interest and to create a sealing engagement between the tissue and the permeable membrane of the optode.

According to a particularly advantageous concept of the invention, during the measurement procedure, the indicator is set into motion within the indicator space in a direction perpendicular to that in which the substance to be analyzed is moving at the other side of the permeable membrane, and most preferably both these perpendicular directions of motion are parallel to the general plane of the permeable membrane. In this way, the concentration gradients on both sides of the permeable membrane are maximum and thus the speed at which the equilibrium condition requisite for accurate and repeatable measurement is established likewise is maximum.

According to yet another concept of the invention, in order to increase the speed of response of the measuring apparatus, the effective surface area of the permeable membrane relative to the volume occupied by the indicator should be made as large as possible. An extreme increase in the ratio of this surface area to this volume can be achieved by encapsulating the indicator, along with magnetic particles, in microcapsules made of the permeable-membrane material, the microcapsules having a diameter of less than ten microns. In that event, a multitude of such indicator microcapsules, each of which in effect constitutes a tiny optode, can be introduced into a branch at one end of a conduit through which the substance to be analyzed is flowing and removed from another branch of the conduit at the other end thereof.

The very great advantage of this expedient is that the component of interest in the substance to be analyzed, in which the microencapsulated indicator is provided, need penetrate only a very small distance into each indicator capsule, so that the ordinary speed of diffusion is more than adequate to assure that all parts of the indicator are penetrated by the component of interest very quickly. Furthermore, the inclusion of magnetic particles in each microcapsule makes it possible to use a magnetic field to effect motion of the indicator capsules relative to the substance to be analyzed, e.g., either to facilitate distribution of the microcapsules within the substance to be analyzed and/or to "steer" the indicator microcapsules—for example to be able to introduce the indicator microcapsules at one location in a conduit carrying the substance to be analyzed and then remove the microcapsules, using mangetic fields, through a branch outlet in the conduit, so that the microcapsules will not enter the main path of travel of the substance to be analyzed.

According to a further concept of the invention, the light-measuring unit of the device is operatively associated, in alternation, with two different portions of the optode, in respective ones of which two different concentrations of the component of interest are prevailing. If the alternation is performed rapidly, the optode does not achieve saturation with respect to the prevailing concentration value; however, the degree of saturation actually achieved is a function of the actual concentration of the component of interest and the effective duration of the measurement, and this functional relationship is well understood in the art. Because the degree of saturation achieved is in accordance with the well known exponential saturation function, the end value of the concentration of the component of interest in the indicator space can be determined from the initial value of this concentration, in conjunction with the value achieved at the end of the measuring period and the duration of the measuring period. This makes it possible to very considerably shorten the duration of the measuring operation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
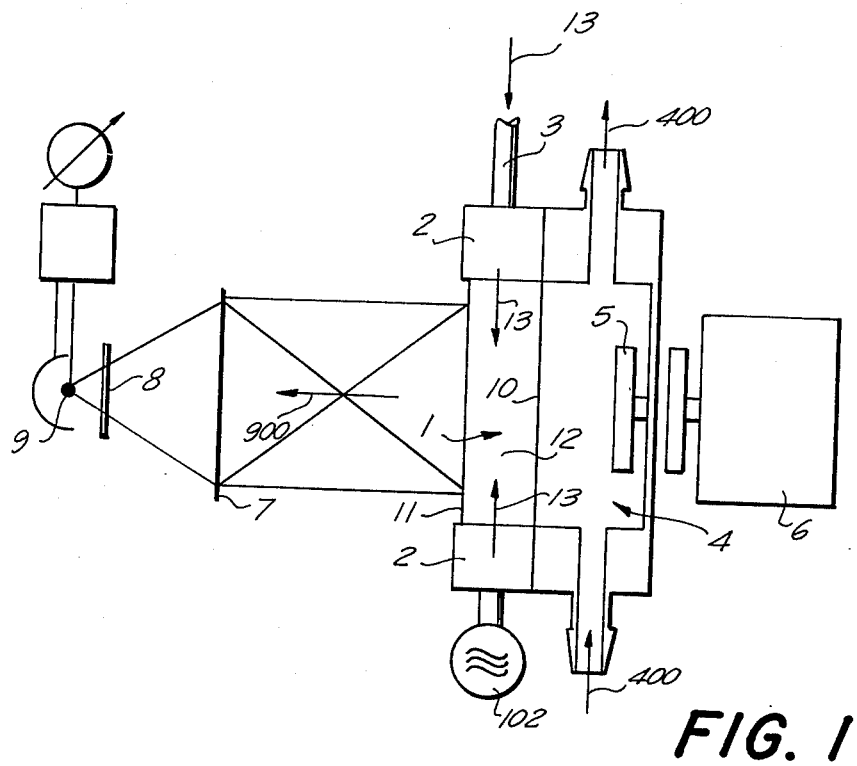
FIG. 1 depicts a first exemplarly embodiment of the invention.

In the embodiment depicted in FIG. 1, an optode 1 comprises a membrane 10 which is permeable for the component of interest in the substance 400 to be analyzed, i.e., the component whose concentration is to be ascertained. For example, the substance 400 to be analyzed may be human blood, and the component of interest oxygen. The optode 1 furthermore comprises a membrane or diaphragm 11 which is transmissive for the radiation to be measured. Intermediate the two membranes 10, 11 is an indicator, for example pyrene butyric acid for the measurement of oxygen concentration in blood.

Excitation radiation 13 is transmitted to the optode by means of a light-conductor element 3, from a conventional monochromator or a source of monochromatic radiation. The light-conductor element 3 is connected to an intermediate optical coupling element 2, which can be made of transparent plastic. The optode 1 and the optical coupling element 2 which surrounds or encloses it are both of circular configuration. The excitation radiation 13 introduced into the coupling element 2 via the lightconductor element 13 is directed radially inward into the indicator space by means of the coupling element 2, from all around the inner periphery of the circular coupling element 2.

In this embodiment, the membrane 10 separates the indicator in optode 1 from a cuvette 4 containing the substance 400 to be analyzed, the cuvette 4 being provided with inlet and outlet conduits for the flow of substance 400 therethrough. In the interior of cuvette 4, there is provided an agitator 5 driven by a motor 6 located external to the cuvette 4. The agitator 5 prevents the formation of too flat a concentration gradient in front of the membrane 10 such as could result from diffusion of the component of interest through the membrane 10 into the indicator.

Because the monochromatic excitation radiation 13 penetrates through the indicator by sweeping alongside the membrane 10, no primary radiation will be developed within the cuvette 4, i.e., because the direction in which the excitation radiation 13 passes through the indicator space is such that it cannot reach the light-measuring unit 9 of the device, and it does not pass through the cuvette 4 and the substance 400 therein. Accordingly, the radiation 900 emitted from the indicator space derives only from the indicator itself and does not include either components attributable to the excitation energy or components attributable to the response which the component of interest and/or the substance to be analyzed might have to the excitation energy and/or to the radiation emitted by the indicator per se. The radiation 900 emitted by the indicator 12 is projected by an optical system 7 through a filter 8 onto the light-measuring unit 9 of the device, this being in other respects conventional.

A mechanical oscillatory-motion generator 102 is mechanicaly coupled to the optode and is operative for setting the indicator 12 therein into oscillatory motion, for the reasons discussed earlier. Preferably, the oscillatory-motion generator 102 is a generator of ultrasonic waves; however, other means of mechanically transmitting oscillatory motion to the indicator gas 12 could also be used. For example, piezoelectric crystals could be disposed on the membranes and energized by oscillatory voltage in order to produce an oscillating or other external deformation of the optode itself. Actually, the transmission of ultrasonic waves by generator 102 will, in itself, to some extent effect external deformation of the optode and thus oscillate the indicator in that sense, too.

In the illustrative embodiment of FIG. 1, for the materials specified above, the permeable membrane 10 can be Teflon having a thickness of about 12 microns. The wavelength of the excitation radiation can be about 326 manometers, and the wavelength of the radiation emitted by the indicator would be 395 nanometers. The velocity of agitation of the indicator can be, for example, about 300-400 cm/min.

Figure 2:
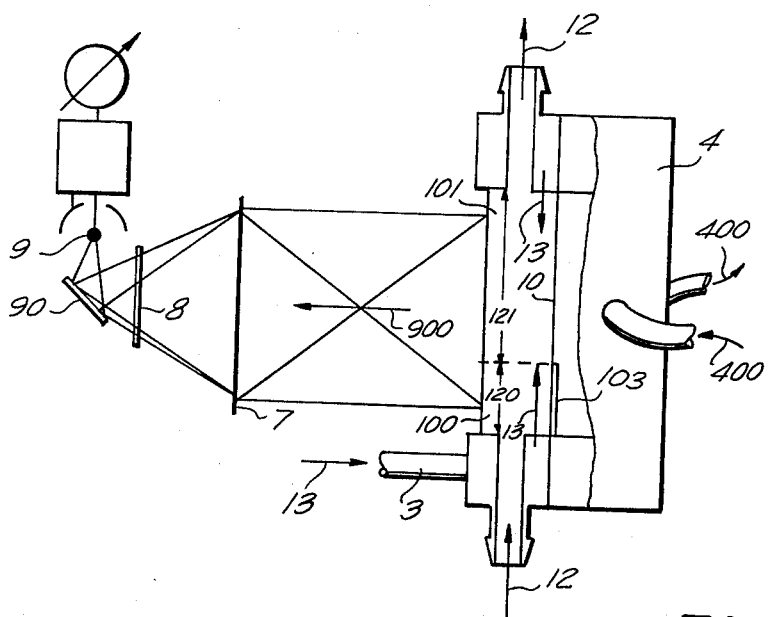
FIG. 2 depicts a second exemplary embodiment of the invention.

FIG. 2 depicts a second exemplary embodiment. Here, the indicator 12 is caused to flow through the optode 1 during the course of the measurement procedure. This flow can, for example, be a circulating flow, i.e., the indicator leaving the outlet of the optode being immediately returned to the inlet thereof, or a non-circulating flow. In this embodiment, too, the substance 400 to be analyzed is located in a cuvette 4, the interior of which is separated from the indicator space by the permeable membrane 10, the cuvette 4 again forming, if desired, a single component together with the optode. In this embodiment, the substance 400 to be analyzed is transmitted through the cuvette 4 through inlet and outlet conduits, in either a circulating or non-circulating flow. As depicted in FIG. 2, the flow directions of the indicator 12 and of the substance 400 to be analyzed are perpendicular to each other, and generally parallel to the plane of permeable membrane 10. This results in the establishment of a very steep concentration gradient on the two sides of membrane 10. This greatly increases the rate at which the component of interest can penetrate through the membrane 10, and thereby inherently shortens the duration of the entire measurement operation.

In the embodiment of FIG. 2, further means are provided, operative for effecting an additional decrease in the time required for the measurement operation. At the infeed zone 120 for indicator 12, there is provided a shield 103—i.e., an element which is not permeable with respect to the component whose concentration is to be measured. Accordingly, as fresh indicator gas 12 is introduced into this infeed zone 120, it will not be loaded by the component of interest, and its spectral response to the excitation radiation 13 will correspond to its isolation from the component of interest. As the indicator gas 12 reaches the zone 121 downstream of infeed zone 120, it combines with the component of interest as the latter penetrates the permeable membrane 10. The indicator will not, when it reaches the outlet zone of the optode, have yet reached saturation.

However, the light-measuring unit 9 of the device is provided with an oscillating mirror 90. Mirror directs onto the light-sensitive surface of unit 9 first the radiation being emitted by the indicator at zone 100 and then the radiation being emitted by the indicator at zone 101, in alternation. The amplitude of the resultant signal produced by light-measuring unit 9 accordingly corresponds to the difference in concentration as between these two extreme zones 100, 101. By extrapolation from these two concentration values, the concentration value which would be assumed if complete saturation had occurred can readily be calculated, because saturation proceeds exponentially; indeed, because each such difference in extreme concentration values can be correlated with the respective complete-saturation value, in general, the read-out of the light-measuring unit 9 can be permanently calibrated accordingly, so that the extrapolation need not actually be performed during use of the apparatus. I.e., the radiation intensity difference as between the two extreme zones 100, 101 is dependent upon and directly correlatable with the concentration of the component of interest in the substance to be analyzed.

Figure 3:
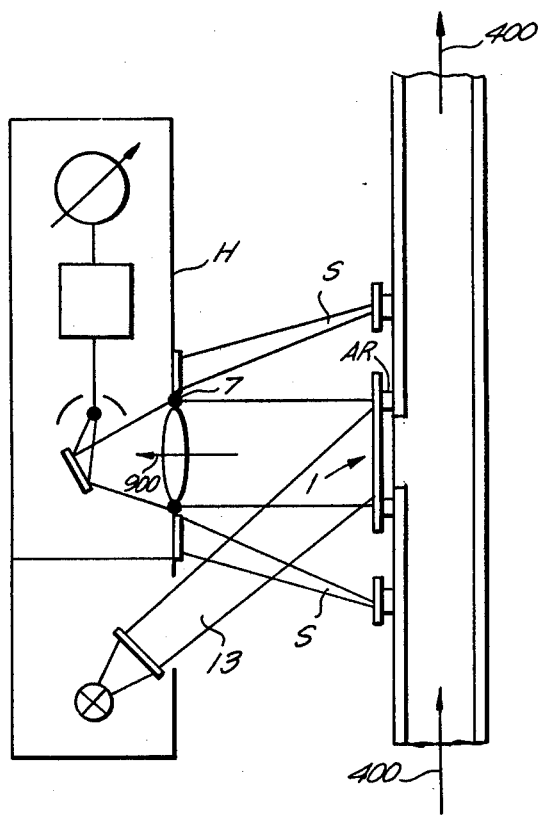
FIG. 3 depicts a third exemplarly embodiment of the invention.

FIG. 3 depicts an embodiment in which a cuvette 4 does not form together with the optode a single structural component. Instead, the optode membrane permeable to the component of interest is provided at its rim with an annular sealing ring AR of adhesive material. The excitation source and the light-measuring unit of the device are housed in a housing H, supported by supports S against a conduit through which the substance 400 to be analyzed flows. The conduit, as shown, is provided with an opening whose configuration corresponds to that of the optode. Accordingly, when the optode is sealed and fixed in place upon this opening, by means of annular sealing ring AR, the component of interest in the flowing substance will permeate through the permeable membrane, as before. In principle, the conduit could be a blood vessel or could be body tissue through which blood is perfused.

Figure 4:
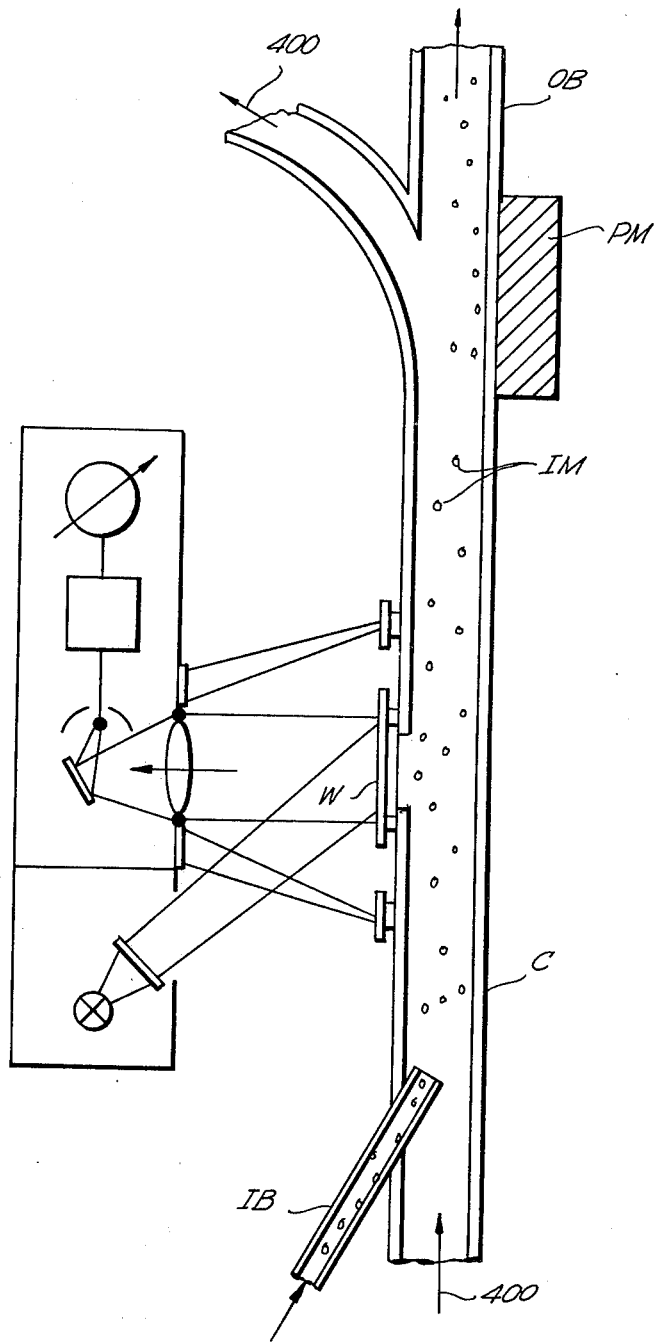
FIG. 4 depicts a fourth exemplary embodiment of the invention.

FIG. 4 depicts an alternative embodiment of particular interest. Here, the permeable-membrane material of the other embodiments is used to form microcapsules IM in which indicator is encapsulated along with magnetic particles, such as very fine iron particles. The diameter of each indicator microcapsule IM is for example about 10 microns. Thus, each 10-micron-diameter microcapsule, in effect, constitutes a tiny optode in itself. An excitation source and light measuring unit are used as in FIG. 3 referred to above. The conduit C through which the substance 400 to be analyzed flows has an opening, across which is applied a transparent window W—i.e., instead of the optode of FIG. 3. The indicator microcapsules IM are fed into the conduit C upstream of the actual measuring location through an infeed branch IB. They are removed from the conduit C via an outfeed branch OB located downstream of the measuring location.

A permanent magnet PM, which as indicated in the drawing is oscillated, pulls the indicator microcapsules IM towards the outfeed branch OB, i.e., so that the microcapsules do no travel with the substance 400, due to the inclusion of the aforementioned magnetic particles within each microcapsule. The oscillatory motion of the permanent magnet PM increases the reliability with which the microcapsules are "steered" into outfeed branch OB.

The great advantage of this embodiment is that the encapsulated indicator is very quickly penetrated by the component of interest, due to the very short penetration depth which each 10-micron-diameter microcapsule presents to the component of interest.

The production of such microcapsules is per se conventional in the art, and is discussed, just for example, in "Microcapsules and Microencapsulation Techniques" by M. H. Gutcho, Chem. Tech. Review 73, Noyes Data Corporation, 1976; and in "Microencapsulation" by J. R. Nixon, Marcel Dekker, Inc., New York, 1976.

It will be understood that each of the elements described above, or two or more together, may also find a useful application in other types of constructions differing from the types described above.

While the invention has been illustrated and described as embodied in the measurement of oxygen in perfused blood, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means setting the indicator in the indicator space into motion within and relative to the indicator space during the measurement operation performed by the apparatus.

2. The apparatus defined in claim 1, the means defining the indicator space being an optode, the means for setting the indicator into motion comprising a mechanical oscillatory-motion generator mechanically coupled to the optode.

3. The apparatus defined in claim 1, including electrical- or magnetic-field-responsive material in the indicator space operative for setting the indicator into motion when subjected to an electrical or magnetic field.

4. The apparatus defined in claim 1, the means defining the indicator space being an optode, the means for setting the indicator into motion comprising means for deforming the optode.

5. A method of optically measuring the concentration of a component of a substance to be analyzed of the type wherein a source of monochromatic excitation radiation is used to excite the indicator contained in an indicator space closed off at the side thereof facing the monochromatic radiation by a radiation-transmissive means and closed off at the side to be brought into contact with the substance to be analyzed by a membrane permeable to the component whose concentration is to be ascertained, the improvement wherein the indicator is set into motion within and relative to the indicator space during the measurement operation.

6. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, means defining a chamber for accommodating the substance to be analyzed and bounded by the permeable membrane, and agitator means in the chamber operative for agitating the substance to be analyzed.

7. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means for setting the substance to be analyzed into convective motion in direction parallel to the membrane to cause the substance to travel across the membrane, the means for setting the substance to be analyzed into motion comprising means for circulating the substance out of and back into a chamber bounded by the permeable membrane.

8. An apparatus for the optical measurement of the concentration of a component of a substance to be analyzed, of the type comprising a source of monochromatic excitation radiation, means defining an indicator space obtaining an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means setting the indicator in the indicator space into motion during the measurement operation performed by the apparatus, the permeable membrane being provided on its rim with adhesive means operative for detachably attaching the permeable membrane to a structure through which the substance to be analyzed is flowing.

9. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means setting the indicator in the indicator space into motion during the measurement operation performed by the apparatus, the means setting the indicator into motion comprising means setting the indicator into motion in a direction parallel to the permeable membrane, further including means for setting the substance to be analyzed into motion in a direction parallel to the permeable membrane but perpendicular to the direction of motion of the indicator.

10. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means setting the indicator in the indicator space into motion during the measurement operation performed by the apparatus, the means defining the indicator space comprising a plurality of permeable-membrane microcapsules encapsulating the indicator and additionally encapsulating magnetic material, the means setting the indicator into motion including magnet means operative for exerting magnetic force on the magnetic material encapsulated within the permeable-membrane microcapsules.

11. An apparatus for the optical measurement of the concentration of a component of a substance to be analyzed, of the type comprising a source of monochromatic excitation radiation, means defining an indicator space containing an indicator excited by the excitation radiation, the side of the means defining the indicator space to be brought into contact with the substance to be analyzed comprising a membrane permeable for the component whose concentration is to be determined, the side of the means defining the indicator space facing the monochromatic excitation radiation being transmissive for the radiation, the improvement wherein the apparatus includes means for setting the substance to be analyzed into convective motion in direction parallel to the membrane to cause the substance to travel across the membrane, means operative for causing two different portions of the indicator to be differently saturated by the component whose concentration is to be measured, and photometric means operative for photometrically ascertaining the respective extents to which said two different portions of the indicator are saturated by the component whose concentration is to be measured.

12. The apparatus defined in claim 11, the photometric means including means operative to alternatively measure the light emitted by the two different portions of the indicator to generate a corresponding difference signal.

13. A method of optically measuring the concentration of a component of a substance to be analyzed of the type wherein a source of monochromatic excitation radiation is used to excite the indicator contained in an indicator space closed off at the side thereof facing the monochromatic radiation by a radiation-transmissive means and closed off at the side to be brought into contact with the substance to be analyzed by a membrane permeable for the component whose concentration is to be ascertained, the improvement wherein the substance to be analyzed is set into convective motion in a direction parallel to the permeable membrane and flows across the permeable membrane while accommodated within a chamber bounded by the permeable membrane using agitator means located in the chamber.

14. A method of optically measuring the concentration of a component of a substance to be analyzed of the type wherein a source of monochromatic excitation radiation is used to excite the indicator contained in an indicator space closed off at the side thereof facing the monochromatic radiation by a radiation-transmissive means and closed off at the side to be brought into contact with the substance to be analyzed by a membrane permeable for the component whose concentration is to be ascertained, the improvement wherein the substance to be analyzed is set into the convective motion in a direction parallel to the permeable membrane and flows across the permeable membrane by repeatedly circulating the substance to be analyzed out of and then back into a chamber bounded by the permeable membrane.

* * * * *